United States Patent
Brattsand et al.

[11] Patent Number: 6,043,236
[45] Date of Patent: Mar. 28, 2000

[54] ESTROGENS

[75] Inventors: Ralph Brattsand; Rikard Holmdahl; Liselotte Jansson; Marjana Loncar, all of Lund; Lars Pettersson, Södra Sandby, all of Sweden

[73] Assignee: Astra Aktiebolag, Sweden

[21] Appl. No.: 08/817,683

[22] PCT Filed: Aug. 20, 1996

[86] PCT No.: PCT/SE96/01028

§ 371 Date: Apr. 23, 1997

§ 102(e) Date: Apr. 23, 1997

[87] PCT Pub. No.: WO97/08188

PCT Pub. Date: Mar. 6, 1997

[30] Foreign Application Priority Data

Aug. 23, 1995 [SE] Sweden .................................. 9502921

[51] Int. Cl.$^7$ .............................. C07J 13/00; A61K 31/56
[52] U.S. Cl. ........................ 514/182; 514/825; 514/903; 552/508; 552/530; 552/533
[58] Field of Search ................................... 552/530, 533, 552/508; 514/182, 825, 903

[56] References Cited

U.S. PATENT DOCUMENTS

| | | | |
|---|---|---|---|
| 4,977,147 | 12/1990 | Jungblut et al. | 514/171 |
| 5,124,321 | 6/1992 | Jungblut et al. | 514/182 |
| 5,371,078 | 12/1994 | Clark et al. | 514/182 |

OTHER PUBLICATIONS

Arnason et al., Effects of Estrogen, Progestin and Combined Estrogen–Progestin Oral Contraceptive Preparations on Experimental Allergic Encephalomyelitis, American Neurological Association Transactions, vol. 94, pp. 54–58, 1969.

Lichtenberger et al., New Synthetic Reactions. Catalytic vs. Stoichiometric Allylic Alkylation. Stereocontrolled Approach to Steroid Side Chain, Journal of the American Chemical Society, vol. 98, No. 2, Jan., 1996.

Vandenbroucke et al., Oral Contraceptives and Rheumatoid Arthritis: Further Evidence for a Preventive Effect, Lancet, pp. 839–842, Oct., 1982.

Walker et al., Influence of Natural and Synthetic Estrogens on the Course of Autoimmune Disease in the NZB/NZW Mouse, Arthritis and Rheumatism, vol. 16, No. 2, pp. 231–239, 1973.

Sally J. Wingave, Reduction in Incidence of Theumatoid Arthritis Associated with Oral Contraceptives, Lancet, pp. 569–571, Mar., 1978.

Trost et al., "Stereocontrolled approach to steroid side chain via organopalladium chemistry. Partial synthesis of 5alpha–cholestanone." J. Amer. Chem. Soc., vol. 100(11), pp. 3435–3443, 1978.

Trost et al., "New synthetic reactions. Catalytic vs. stoichiometric allylic alkylation. Stereocontrolled approach to steroid side chain." J. Amer. Chem. Soc., vol. 98(2), pp. 630–632, 1976.

*Primary Examiner*—José G. Dees
*Assistant Examiner*—Barbara Badio
*Attorney, Agent, or Firm*—Fish & Richardson P.C.

[57] ABSTRACT

Compounds of the formula I

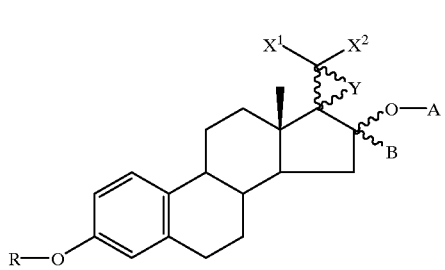

a process for their preparation, their use in the treatment of autoimmune disorders as well as new intermediates for their preparation.

16 Claims, No Drawings

ESTROGENS

This application is a 371 of PCT/SE96/01028 filed Aug. 20, 1996.

FIELD OF THE INVENTION

The present invention relates to novel compounds which are steroidal estrogens, to methods for their preparation, their use and pharmaceutical compositions comprising the novel compounds. The novel compounds are useful for the treatment of inflammatory and immunologic disorders, especially for the treatment of autoimmune disorders. The compounds according to the present invention are especially preferred for the treatment of rheumatoid arthritis (RA) and multiple sclerosis (MS).

BACKGROUND AND PRIOR ART

Sex hormones have since long been known to ameliorate arthritic symptoms in chronic arthritis during pregnancy, see for example Hench P. S. "The ameliorating effect of pregnancy on chronic atrophic arthritis, fibrositis, and intermittent hydrathrosis", Mayo Clin. Proc., 13, 161–167, 1983. The use of oral contraceptives in patients with rheumatoid arthritis (RA) have proven to decrease the incidence of RA, see Wingrave S. J., Kay C. R. "Reduction in incidence of rheumatoid arthritis associated with oral contraceptives", Lancet, 569–571, 1978; and Vandenbroucke J. P. et al., "Oral contraceptives and rheumatoid arthritis: Further evidence for a preventive effect", Lancet 839–842, 1982.

In JP 268575/1990 estradiol derivatives are described, but the substituents in 17-position are completely different from the substituents in 17-position of the present application. The problem underlying the invention described in JP 268575/1990 is to find compounds against osteoporosis, said compounds having an excellent bone resorption inhibiting action without showing side effects such as risk for genital cancer etc. known in the art for estrogens.

The problem underlying the present invention is to develop novel steroidal estrogens with high anti-inflammatory and immunosuppressive effects, but with low "sex hormonal" activities. The steroidal estrogens known in the prior art, have the disadvantages that they influence genital and breast tissues, thereby conferring adverse effects such as endometrial and breast cancers if given in too high amounts.

The problem mentioned above has been solved by developing new steroidal estrogens according to the formula I, as will be described in the following.

SUMMARY OF THE INVENTION

The object of the present invention is to provide novel compounds, which are steroidal estrogens, and a method for their preparation.

Another object of the present invention is the use of the novel compounds for the treatment of inflammatory and immunologic diseases, especially for the treatment of autoimmune diseases.

Still another object of the invention is a pharmaceutical composition comprising a compound of the invention as active ingredient, optionally in the presence of a pharmaceutically acceptable carrier.

The novel compounds of the present invention are defined by the general formula I

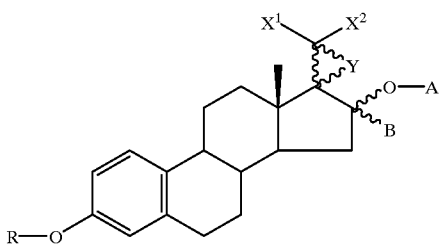

wherein
A is hydrogen, $C_2$–$C_{18}$ alkanoyl, ($C_6$ aryl)carbonyl, $C_2$–$C_{19}$ alkoxycarbonyl, ($C_6$ aryloxycarbonyl, or a protecting group;
B is hydrogen, methyl, or ethyl;
R is hydrogen, a straight, branched or cyclic $C_1$–$C_6$ alkyl, $C_2$–$C_{18}$ alkanoyl, ($C_6$ aryl)carbonyl, $C_2$–$C_{19}$ alkoxycarbonyl, ($C_6$ aryloxy)carbonyl, or a protecting group;
$X^1$ is hydrogen, methyl, ethyl, or halogen;
$X^2$ is hydrogen, methyl, ethyl, or halogen; and
Y is methylene or a single bond;
the compounds
(17E)-16α-Acetoxy-3-methoxy-19-norpregna-1,3,5(10),17(20)-tetraene;
(17E)-16α-hydroxy-3-methoxy-19-norpregna-1,3,5(10),17(20)-tetraene; and
(17E)-16β-hydroxy-3-methoxy-19-norpregna-1,3,5(10),17(20)-tetraene
being excluded.

Within the scope of the invention are also pharmaceutically acceptable salts of the compounds of the formula I.

Preferred compounds of the invention are compounds of the formula I wherein
A is hydrogen or $C_2$–$C_6$ alkanoyl;
B is hydrogen or methyl;
R is hydrogen, a straight, branched or cyclic $C_1$–$C_6$ alkyl, $C_2$–$C_{18}$ alkanoyl, ($C_6$ aryl)carbonyl, $C_2$–$C_{19}$ alkoxycarbonyl, ($C_6$ aryloxy)carbonyl, or a protecting group;
$X^1$ is hydrogen, methyl, or fluorine;
$X^2$ is hydrogen, methyl, or fluorine; and
Y is methylene or a single bond.

Particularly preferred compounds of the invention are compounds according to the formula I wherein
A is hydrogen or $C_2$–$C_6$ alkanoyl;
B is hydrogen;
R is hydrogen, a straight, branched or cyclic $C_1$–$C_6$ alkyl, $C_2$–$C_{19}$ alkanoyl or ($C_6$ aryl)carbonyl;
$X^1$ is hydrogen or fluorine;
$X^2$ is hydrogen or fluorine; and
Y is a single bond or a methylene group.

Examples of protecting groups are benzyl, THP (tetrahydropyranyl), methoxymethyl, dimethylthexylsilyl, and tert-butyldimethylsilyl. A preferred protecting group is dimethylthexylsilyl.

The most preferred compound of the invention is 3,16α-dihydroxy-17-methylene-estra-1,3,5(10)triene.

The novel steroidal estrogens according to the invention are characterized by high anti-inflammatory and immunosuppressive effects, and low "sex hormonal" activities. Thus the novel steroidal estrogens have low proliferative effects on genital tissues, which reduces the likelihood of adverse effects such as endometrial cancers.

The novel steroidal estrogens according to the invention are useful for the treatment of inflammatory and immunologic disorders, especially for the treatment of autoimmune disorders.

The steroidal estrogens according to the present invention are excellent for the treatment of rheumatoid arthritis (RA) and multiple sclerosis (MS).

DETAILED DESCRIPTION OF THE INVENTION

Methods of Preparation

Common to all starting materials for the preparation of compounds of the formula I is the presence of a 17-keto group. The introduction of the 17-alkylidene group can be achieved by a Wittig-type reaction (see e.g. Krubiner, A. M. et al. J. Org. Chem., 1966, 31, 24) whereby a compound of the formula II

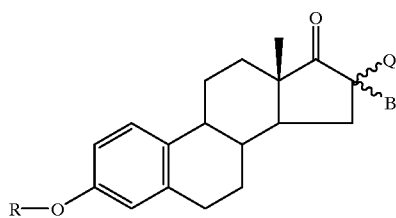

wherein

A is hydrogen, $C_2$–$C_{18}$ alkanoyl, ($C_6$ aryl)carbonyl, $C_2$–$C_{19}$ alkoxycarbonyl, ($C_6$ aryloxy)carbonyl, or a protecting group;

B is hydrogen, methyl, or ethyl;

R is hydrogen, a straight, branched or cyclic $C_1$–$C_6$ alkyl, $C_2$–$C_{18}$ alkanoyl, ($C_6$ aryl)carbonyl, $C_2$–$C_{19}$ alkoxycarbonyl, ($C_6$ aryl)oxycarbonyl, or a protecting group; and Q is (O—A) or hydrogen, wherein O is oxygen and A is as defined above;

the 3-O-position being optionally protected is reacted with a phosphorous ylide or with the salt of a stabilized alkylphosphonate, optionally followed by the reduction of the adduct when a stabilized alkyl phosphonate is used, giving a compound of the formula III

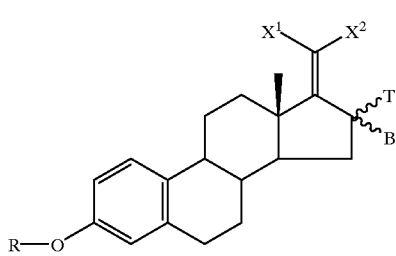

wherein

A is hydrogen, $C_2$–$C_{18}$ alkanoyl, ($C_6$ aryl)carbonyl, $C_2$–$C_{19}$ alkoxycarbonyl, ($C_6$ aryloxycarbonyl, or a protecting group;

B is hydrogen, methyl, or ethyl;

R is hydrogen, a straight, branched or cyclic $C_1$–$C_6$ alkyl, $C_2$–$C_{18}$ alkanoyl, ($C_6$ aryl)carbonyl, $C_2$–$C_{19}$ alkoxycarbonyl, ($C_6$ aryloxy)carbonyl, or a protecting group; and $X^1$ is hydrogen, methyl, ethyl or halogen; and $X^2$ is hydrogen, methyl, ethyl or halogen.

T is (O—A) or hydrogen, wherein O is oxygen and A is as defined above;

the 3-O-position being optionally protected.

The above given definition that Q and T is (O—A) or hydrogen respectively, means that the 16-position may be protected or unprotected.

The reaction is preferably carried out in a polar solvent such as DMSO, THF or dimethoxyethane, and the temperature is preferably in the range ambient temperature to the boiling point of the solvent.

When stabilized alkylphosphonates are used, the substituents $X^1$ and $X^2$ in formula III may be carbonyl moieties, such as an ester or ketone, which can be reduced to an alcohol, and further reduced to an alkyl group.

The 16-OA functionality may be present in the starting material or introduced at a later stage. If not present in the starting material, the 16-OA functionality is introduced via an oxidation such as a $SeO_2$-oxidation (Sharpless, K. B. et al. Aldrichimica Acta, 1979, 12, 63), whereby a compound of the formula IV

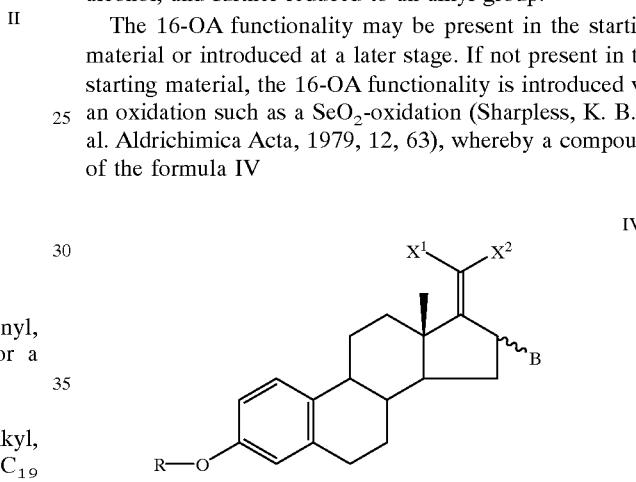

wherein

B is hydrogen, methyl, or ethyl;

R is hydrogen, a straight, branched or cyclic $C_1$–$C_6$ alkyl, $C_2$–$C_{18}$ alkanoyl, ($C_6$ aryl)carbonyl, $C_2$–$C_{19}$ alkoxycarbonyl, ($C_6$ aryloxy)carbonyl, or a protecting group; and Each of $X^1$ and $X^2$ is independently hydrogen, methyl, or ethyl;

is subjected to a $SeO_2$-oxidation, giving the 16α-OH compound of the formula V selectively (Trost, B. M. et al. J. Am. Chem. Soc., 1978, 100, 3435) together with the 16-keto compound of the formula VI

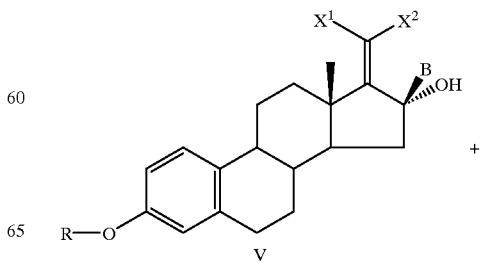

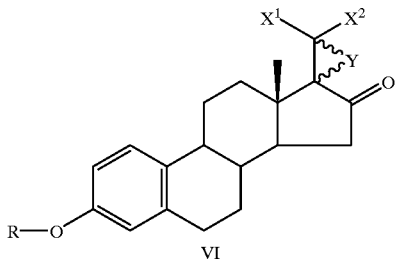

wherein
B is hydrogen, methyl, or ethyl; R is hydrogen, a straight, branched or cyclic $C_1$–$C_6$ alkyl, $C_2$–$C_{18}$ alkanoyl, ($C_6$ aryl)carbonyl, $C_2$–$C_{19}$ alkoxycarbonyl, ($C_6$ aryloxy)carbonyl, or a protecting group;
Each of $X^1$ and $X^2$ is independently hydrogen, methyl or ethyl; and
Y is a single bond.

In a compound of the formula VI, $X^1$ and $X^2$ may also each independently be selected from a halogen, and Y may also be selected from methylene.

$SeO_2$ is preferably used in catalytic amounts together with tertbutylhydroperoxide as a co-oxidant in toluene at ambient temperature.

These first reaction steps can be performed on either 3-O-unprotected (R=H) or protected (R=e.g. $R_3Si$, tetrahydropyranyl (THP), alkyl or benzyl) material. The introduction of the protecting group is achieved by standard methods (Protective groups in organic synthesis, Green, T. W. and Wuts, P. G. M., 2nd ed., Wiley). Thus, the free phenol can be protected as a dimethylthexylsilyl ether using dimethylthexylsilyl chloride as silylating reagent and imidazole as base in the solvent dimethylformamide (DMF) at ambient temperature.

The 16-keto compound of the formula VI is further subjected to a nucleophile, such as a Grignard reagent in an inert solvent, such as $Et_2O$ or THF, or alternatively reduced, e.g. with $NaBH_4$ or $LiAlH_4$, giving the 16β-hydroxy compound of the formula I wherein Y is a single bond.

The cyclopropane moiety is introduced by reacting a compound of the formula I or VI with a cyclopropanation reagent, whereby the alkene moiety of the compound of the formula I or VI wherein Y is a single bond, is reacted with a cyclopropanation reagent, optionally in the presence of a metal promotor, giving a compound of the formula I or of the formula VI (Y=methylene) respectively. One preferred cyclopropanation reaction is the Simmons-Smith reaction, using a 1,1-dihalo compound in the presence of activated Zn, preferably in etheral solvents such as dimethoxyethane. The cyclopropanation reaction of choice for the introduction of the cyclopropane moiety will be clear for one skilled in the art (Advanced Organic Chemistry: reactions, mechanisms and structure, J. March, 4th ed., p 870 ff., Wiley).

The phenolic 3-OH group may be protected, e.g., as a silylether (or as an alkylether, a benzylether, or an acetal, like THP-ether) throughout the reaction sequences. Thus, the unprotected 16-OH can then be reacted with activated ester derivatives, such as ester halides or anhydrides, to give 16-O-monoacylated derivatives.

The 3-O-silyl ether can be cleaved by fluoride ion (e.g. $Bu_4NF(H_2O)_3$ in THF) or by acid or base treatment to give the free phenol derivatives (van Look, G., "Silylating Agents", Fluka Chemie, 1988). The 3-O-monoacylated derivatives can also be regioselectively prepared, e.g. by acylating the tetrabutylammonium phenolate generated in the $Bu_4NF$-desilylation step by acylating agents like acid chlorides or anhydrides, or by acylating the 3,16-diol by the method of Illi V. O., Tetrahedron Lett. 1979, p. 2431 using acid chlorides as acylating reagents in dioxane, NaOH as base and catalytic amounts of tetrabutylammonium hydrogen sulfate.

EXAMPLES

The invention will now be described in more detail by the following examples which are not to be construed as limiting the invention.

In the examples column chromatography separations were performed using Merck $SiO_2$ 60 (0.040–0.063 mm) silica gel with heptane-EtOAc mixtures as eluents.

TLC analyses were performed on Merck $SiO_2$ 60 F254 precoated aluminium sheets: $R_f$ values were measured in heptane-EtOAc eluent mixtures and the spots were visualized by charring with 10% aqueous $H_2SO_4$.

Melting points were determined with a Weitz Wetzlar microscope and are uncorrected.

MS(FAB) spectra were recorded with a VG Analytical Autospec-Q spectrometer. NMR spectra were recorded with a Varian VXR (300 MHz) or a Varian Unity+ (500 MHz).

Dry solvents were prepared by drying p.a. (pro analysis) grade solvents over molecular sieves (4 Å).

General Procedure for 16α-hydroxylation of 17-alkylidenes (Procedure A):

$SeO_2$ (11 mg, 0.1 mmol) was added to a solution of the 17-alkylidene (1.0 mmol) and tert-butylhydroperoxide (0.67 ml, ca 2.0 mmol, ca 3.0 M "phase separated" in toluene, Sharpless, K. B. et al. Aldrichimica Acta, 1979, 12, 63) in toluene (1.0 ml). The reaction mixture was stirred over night and thereafter diluted with $Et_2O$ (50 ml). $FeSO_4$ (10 ml, 1 M) was added and after 30 min stirring the organic phase was separated and washed with brine (2×30 ml). The organic phase was dried over $Na_2SO_4$ and concentrated at reduced pressure. The residue was purified by column chromatography to give the 17-alkylidene-16α-hydroxy compound (yields ca 40–60%) and the 17-alkylidene-16-keto compound (yields ca 20–30%).

General Procedure for 3-O-Desilylation of 3-O-Dimethylthexylsilyl Ether Protected 3-hydroxy-estra-1,3,5(10)-trienes (Procedure B):

$NBu_4F \cdot (H_2O)_3$ (1.1 mmol) was added to a solution of the 3-dimethyl-thexylsilyl ether protected 3-hydroxy-estra-1,3,5(10)-triene (1.0 mmol) in dry THF (1.0 mL). The reaction mixture was stirred for 3 min and thereafter quenched by adding AcOH (1.5 mmol). Concentration at reduced pressure was followed by purification on column chromatography. Alternatively, for larger scale synthesis, a typical work up (dilution with $Et_2O$, washing with water, drying, and concentration) may precede the column chromatography.

Silylations were performed according to the Corey procedure (Corey, E. J., Venkateswarlu, A. J. Am. Chem. Soc. 1972, 94, 6190) with dimethyl-thexyl chlorosilane (1.2 mol eq.) as silylating agent and imidazole (2.5 mol eq.) as base in DMF as solvent. Usual work-up (dilution with $Et_2O$, washing with water, drying, and concentration) followed by column chromatography provided the products in essentially quantitative yields.

Examples 1–2
3,16α-Dihydroxy-17-methylene-estra-1,3,5(10)-triene

Prepared from 3-hydroxy-17-methylene-estra-1,3,5(10)-triene (83% from estrone, Peters, R. H. et al. J. Med. Chem. 1989, 32, 1642) according to Procedure A.

Also prepared from 3,16α-dihydroxy-17-methylene-estra-1,3,5(10)-triene, 3-dimethyl-thexylsilyl ether (Example 5) according to Procedure B.

Yield: 356 mg (92%)
$R_f$ (2:1)=0.20
mp 245–50° C.
MS(FAB): m/z=284 ($M^+$)
$^1$H NMR (CDCl$_3$) δ 0.83 (s, 3H, H-18), 4.53 (s, 1H, phenol), 4.72 (m, 1H, H-16), 4.93 (d, 1H, J=2.1 Hz, =CH$_2$), 5.08 (d, 1H, J=1.4 Hz, =CH$_2$), 6.57 (d, 1H, J=2.8 Hz, H-4), 6.63 (dd, 1H, J=2.8 Hz, 8.3 Hz, H-2), 7.17 (d, 1H, J=8.3 Hz, H-1).

Example 3

3-Hydroxy-17-keto-estra-1,3,5(10)-triene, 3-O-dimethylthexylsilyl ether

Prepared from 3-hydroxy-17-keto-estra-1,3,5(10)-triene (estrone) by silylation using the Corey procedure.

Yield: 29.3 g (94%)
$R_f$ (10:1)=0.10
$^1$H NMR (CDCl$_3$) δ 0.22 (s, 6H, —SiMe$_2$—), 0.91 (s, 3H, H-18), 0.94 (s, 6H, thexyl), 0.94 (d, 6H, J=6.6 Hz, thexyl), 6.56 (d, 1H, J=2.7 Hz, H-4), 6.62 (dd, 1H, J=2.7 Hz, 8.3 Hz, H-2), 7.12 (d, 1H, J=8.3 Hz, H-1).

Example 4

3-Hydroxy-17-methylene-estra-1,3,5(10)-triene, 3-O-dimethylthexylsilyl ether

Prepared from 3-hydroxy-17-methylene-estra-1,3,5(10)-triene (83% from estrone, Peters, R. H. et al. J. Med. Chem. 1989, 32, 1642) by silylation using the Corey procedure.

Yield: 22.4 g (99%)
$R_f$ (8:1)=0.18
$^1$H NMR (CDCl$_3$) δ 0.22 (s, 6H, —SiMe$_2$—), 0.82 (s, 3H, H-18), 0.94 (s, 6H, thexyl), 0.94 (d, 6H, J=6.6 Hz, thexyl), 4.67 (s, 2H, =CH$_2$), 6.55 (d, 1H, J=2.8 Hz, H-4), 6.61 (dd, 1H, J=2.8 Hz, 8.3 Hz, H-2), 7.14 (d, 1H, J=8.3 Hz, H-1).

Example 5

3,16α-Dihydroxy-17-methylene-estra-1,3,5(10)-triene, 3-O-dimethyl-thexylsilyl ether Prepared from 3-hydroxy-17-methylene-estra-1,3,5(10)-triene, 3-O-dimethyl-thexylsilyl ether according to procedure A.

Yield: 5.07 g (59%)
$R_f$ (5:1)=0.29
$^1$H NMR (CDCl$_3$) δ 0.22 (s, 6H, —SiMe$_2$—), 0.83 (s, 3H, H-18), 0.94 (s, 6H, thexyl), 0.94 (d, 6H, J=6.6 Hz, thexyl), 4.71 (m, 1H, H-16), 4.92 (d, 1H, J=2.2 Hz, =CH$_2$), 5.08 (d, 1H, J=1.7 Hz, =CH$_2$), 6.55 (d, 1H, J=2.7 Hz, H-4), 6.61 (dd, 1H, J=2.7 Hz, 8.3 Hz, H-2), 7.13 (d, 1H, J=8.3 Hz, H-1).

This reaction also provided the compound of Example 6 below.

Example 6

3-Hydroxy-16-keto-17-methylene-estra-1,3,5(10)-triene, 3-O-dimethyl-thexylsilyl ether See under Example 5 regarding the synthesis.

Yield: 1.54 g (18%)
$R_f$ (5:1)=0.56
$^1$H NMR (CDCl$_3$) δ 0.22 (s, 6H, —SiMe$_2$—), 0.94 (s, 6H, thexyl), 0.94 (d, 6H, J=7.0 Hz, thexyl), 0.99 (s, 3H, H-18), 5.07 (s, 1H, =CH$_2$), 5.84 (s, 1H, =CH$_2$), 6.56 (d, 1H, J=2.5 Hz, H-4), 6.63 (dd, 1H, J=2.5 Hz, 8.3 Hz, H-2), 7.13 (d, 1H, J=8.3 Hz, H-1).

Example 7

3,16β-Dihydroxy-17-methylene-estra-1,3,5(10)-triene, 3-O-dimethylthexylsilyl ether CeCl$_3$ (283 mg, 1.15 mmol) was added to a solution of 3-hydroxy-17-methylene-16-keto-estra-1,3,5(10)-triene, 3-dimethyl-thexylsilyl ether (488 mg, 1.15 mmol) in dry THF (12 ml) under N$_2$. The slurry was stirred for 5 min and then LiAlH$_4$ (44 mg, 1.15 mmol) was added. The reaction mixture was stirred at room temperature for 15 min, then quenched with 1 M HCl and partitioned in Et$_2$O/water. The organic phase was washed with aq. NaHCO$_3$ (sat.) and brine, dried over Na$_2$SO$_4$ and concentrated at reduced pressure. The residue was purified by column chromatography (heptane-EtOAc, 5:1) to give the titel compound (220 mg, 45%) as a white solid.

$R_f$ (5:1)=0.16
$^1$H NMR (CDCl$_3$) δ 0.22 (s, 6H, —SiMe$_2$—), 0.94 (s, 6H, thexyl), 0.94 (d, 6H, J=7.0 Hz, thexyl), 1.00 (s, 3H, H-18), 4.55 (m, 1H, H-16), 4.92 (s, 1H, =CH$_2$), 5.08 (s, 1H, =CH$_2$), 6.55 (d, 1H, J=2.7 Hz, H-4), 6.61 (dd, 1H, J=2.7 Hz, 8.3 Hz, H-2), 7.13 (d, 1H, J=8.3 Hz, H-1).

Example 8

3,16β-Dihydroxy-17-methylene-estra-1,3,5(10)-triene

Prepared from 3-hydroxy-17-methylene-estra-1,3,5(10)-triene, 3-O-dimethyl-thexylsilyl ether according to procedure B.

Yield: 46 mg (85%)
$R_f$ (1:1)=0.42
mp 229–35° C.
MS(FAB): m/z=284 ($M^+$)
$^1$H NMR (CDCl$_3$) δ 1.00 (s, 3H, H-18), 4.53 (m, 1H, H-16), 4.94 (d, 1H, J=1.8 Hz, =CH$_2$), 5.08 (d, 1H, J=1.8 Hz, =CH$_2$), 6.56 (d, 1H, J=2.7 Hz, H-4), 6.64 (dd, 1H, J=2.7 Hz, 8.5 Hz, H-2), 7.16 (d, 1H, J=8.5 Hz, H-1).

Example 9

3,16β-Dihydroxy-16α-methyl-17-methylene-estra-1,3,5(10)-triene, 3-O-dimethylthexylsilyl ether A solution of 3-hydroxy-17-methylene-16-keto-estra-1,3,5(10)-triene, 3-dimethylthexylsilyl ether (108 mg, 0.25 mmol) in dry Et$_2$O (2 mL) was added to MeMgI (1 mmol, 1M in Et$_2$O) at 0° C. under N$_2$. The reaction mixture was stirred at room temperature over night, then quenched with 1 M HCl and partitioned in Et$_2$O/water. The organic phase was washed with aq. NaHCO$_3$ (sat.) and brine, dried over Na$_2$SO$_4$ and concentrated at reduced pressure. The residue was purified by column chromatography (heptane-EtOAc, 8:1) to give the title compound (40 mg, 37%) as a white solid.

$R_f$ (5:1)=0.21
$^1$H-NMR (CDCl$_3$) δ 0.22 (s, 6H, —SiMe$_2$—), 0.94 (s, 6H, thexyl), 0.94 (d, 6H, J=7.0 Hz, thexyl), 1.03 (s, 3H, H-18), 1.41 (s, 3H, 16-Me), 4.82 (s, 1H, =CH$_2$), 5.06 (s, 1H, =CH$_2$), 6.55 (d, 1H, J=2.7 Hz, H-4), 6.61 (dd, 1H, J=2.7 Hz, 8.3 Hz, H-2), 7.11 (d, 1H, J=8.3 Hz, H-1).

Example 10

3,16β-Dihydroxy-16α-methyl-17-methylene-estra-1,3,5(10)-triene

Prepared from 3,16β-dihydroxy-16α-methyl-17-methylene-estra-1,3,5(10)-triene, 3-O-dimethyl-thexylsilyl ether according to procedure B.

Yield: 12 mg (93%)
$R_f$ (2:1)=0.22
mp 237–39° C.
MS-FAB: m/z=298 ($M^+$)
$^1$H NMR (CDCl$_3$) δ 1.03 (s, 3H, H-18), 1.41 (s, 3H, 16-Me), 4.51 (s, 1H, phenol), 4.83 (s, 1H, =CH$_2$), 5.07 (s, 1H, =CH₂), 6.57 (d, 1H, J=2.8 Hz, H-4), 6.63 (dd, 1H, J=2.8 Hz, 8.3 Hz, H-2), 7.16 (d, 1H, J=8.3 Hz, H-1).

Example 11

3,16α-Dihydroxy-17-(1',2'-ethylene)-estra-1,3,5(10)-triene, 3-O-dimethyl-thexylsilyl ether A slurry of Zn powder (280 mg, 4.28 mmol) in dry dimethoxyethane (DME, 4.0 ml) under N₂ was activated by ultra sound treatment for 1.5 h. A solution of 3,16α-dihydroxy-17-methylene-estra-1,3,5(10)-triene, 3-O-dimethyl-thexylsilyl ether (500 mg, 1.17 mmol) in dry DME (8.0 mL) was added and the temperature was raised to reflux temperature (ca 90° C. in oil bath). CH₂I₂ (390 ml, 4.83 mmol) was added dropwise and the reaction mixture was stirred at reflux temperature over night. After cooling the reaction mixture was partitioned in EtOAc/NH₄Cl (aq., sat.). The organic phase was washed with H₂O, dried over Na₂SO₄ and concentrated at reduced pressure. The residue was purified by column chromatograph (heptane-EtOAc, 8:1) to give the title compound (280 mg, 54%).

$R_f$ (5:1)=0.28

¹H NMR (CDCl₃) δ 0.22 (s, 6H, —SiMe₂—), 0.50, 0.72 (2m, 4H, 17-ethylene), 0.82 (s, 3H, H-18), 0.94 (s, 6H, thexyl), 0.94 (d, 6H, J=7.0 Hz, thexyl), 4.19 (m, 1H, H-16), 6.56 (d, 1H, J=2.7 Hz, H-4), 6.62 (dd, 1H, J=2.7 Hz, 8.3 Hz, H-2), 7.12 (d, 1H, J=8.3 Hz, H-1).

Example 12

3,16α-Dihydroxy-17-(1',2'-ethylene)-estra-1,3,5(10)-triene

Prepared from 3,16α-dihydroxy-17-(1',2'-ethylene)-estra-1,3,5(10)-triene, 3-O-dimethylthexylsilyl ether according to procedure B.

Yield: 50 mg (74%)

$R_f$ (5:1)=0.10 mp 227–32° C.

MS-FAB: m/z=298 (M⁺)

¹H NMR ((CD₃)₂SO) δ 0.24–0.40, 0.65 (2m, 4H, 17-ethylene), 0.76 (s, 3H, H-18), 4.08 (m, 1H, H-16), 4.35 (d, 1H, J=7.1 Hz, 16-OH), 6.44 (s, 1H, H-4), 6.50 (d, 1H, J=8.6 Hz, H-2), 7.02 (d, 1H, J=8.6 Hz, H-1), 9.00 (broad s, 1H, 3-OH).

Example 13

3-Hydroxy-17-keto-16α-methyl-estra-1,3,5(10)-triene, 3-O-dimethylthexylsilyl ether Lithium diisopropylamide (2.8 ml, 4.2 mmol, 1.5 M THF-complex in c-hexane) was added to a solution of 3-hydroxy-17-keto-estra-1,3,5(10)-triene, 3-O-dimethylthexylsilyl ether (1.50 g, 3.63 mmol) in dry THF (6 ml) under N₂ at 0° C. After stirring for 1 h the temperature was lowered to −78° C. and MeI (270 μl, 4.3 mmol) was added. The reaction mixture was stirred at −78° C. for 5 h, then at ambient temperature over night and was then partitioned in EtOAc/H₂O. The organic phase was washed with brine, dried over Na₂SO₄ and concentrated at reduced pressure. The residue was purified by column chromatography (heptane-EtOAc, 20:1) to give the title compound (800 mg, 52%).

$R_f$ (20:1)=0.23

¹H NMR (CDCl₃) δ 0.22 (s, 6H, —Si(CH₃)₂—), 0.94 (s, 3H, H-18), 0.94 (s, 6H, thexyl), 0.94 (d, 6H, J=6.8 Hz, thexyl), 1.14 (d, 1H, J=7.8 Hz, 16-Me), 6.58 (d, 1H, J=2.4 Hz, H-4), 6.62 (dd, 1H, J=2.4 Hz, 8.3 Hz, H-2), 7.13 (d, 1H, J=8.3 Hz, H-1).

Example 14

3-Hydroxy-16α/β-methyl-17-methylene-estra-1,3,5(10)-triene, 3-O-dimethylthexylsilyl ether Potassium tert-butoxide (73 mg, 0.65 mmol) was added to a solution of methyltriphenyl-phosphonium bromide (300 mg, 0.84 mmol) in dry DMSO (1.8 ml) under N₂. After stirring for 20 min the temperature was raised to 75° C. and a solution of 3-hydroxy-17-keto-16α-methyl-estra-1,3,5(10)-triene, 3-O-dimethylthexylsilyl ether (298 mg, 70 mmol) in dry THF (1.5 ml) was added. The reaction mixture was stirred at 75° C. for 1.5 h and was then partitioned in Et₂O/H₂O. The organic phase was washed with H₂O, dried over Na₂SO₄, and concentrated at reduced pressure. The residue was purified by column chromatography (heptane) to give the title compound as a ca 1:1 epimeric mixture (85 mg, 28%).

$R_f$ (heptane)=0.24

¹H NMR (CDCl₃) δ 0.22 (s, 6H, —Si(CH₃)₂—), 0.84, 0.94 (2s, 3H, H-18), 0.94 (s, 6H, thexyl), 0.94 (d, 6H, J=6.8 Hz, thexyl), 1.10, 1.19 (2d, 3H, J=7.1 Hz, 16-Me), 4.68, 4.73 (2m, 2H, Hz, =CH₂), 6.56 (d, 1H, J=2.2 Hz, H-4), 6.62 (dd, 1H, J=2.2 Hz, 8.3 Hz, H-2), 7.13 (d, 1H, J=8.3 Hz, H-1).

Example 15

3,16α-Dihydroxy-16α,β-methyl-17-methylene-estra-1,3,5(10)-triene, 3-O-dimethylthexylsilyl ether Prepared from 3-hydroxy-16α,β-methyl-17-methylene-estra-1,3,5(10)-triene, 3-O-dimethyl-thexylsilyl ether according to procedure A.

Yield: 35 mg (40%)

$R_f$ 10:1)=0.10

¹H NMR (CDCl₃) δ 0.22 (s, 6H, —Si(CH₃)₂—), 0.87 (s, 3H, H-18), 0.94 (s, 6H, thexyl), 0.94 (d, 6H, J=6.8 Hz, thexyl), 1.48 (s, 3H, 16-Me), 4.85, 5.09 (2s, 2H, =CH₂), 6.55 (d, 1H, J=2.4 Hz, H-4), 6.61 (dd, 1H, J=2.4 Hz, 8.3 Hz, H-2), 7.13 (d, 1H, J=8.3 Hz, H-1).

Example 16

3,16α-Dihydroxy-16β-methyl-17-methylene-estra-1,3,5 (10)-triene

Prepared from 3,16α-dihydroxy-16β-methyl-17-methylene-estra-1,3,5(10)-triene, 3-O-dimethyl-thexylsilyl ether according to procedure B.

Yield: 56 mg (78%)

$R_f$ (1:1)=0.47 mp 238–243° C.

MS(FAB): m/z=298 (M⁺)

¹H NMR (CDCl₃) δ ¹H NMR (CDCl₃) δ 0.87 (s, 3H, H-18), 1.49 (s, 3H, 16-Me), 4.53 (s, 1H, phenol), 4.86 (s, 1H, =CH₂), 5.10 (s, 1H, =CH₂), 6.57 (d, 1H, J=2.4 Hz, H-4), 6.64 (dd, 1H, J=2.4 Hz, 8.3 Hz, H-2), 7.18 (d, 1H, J=8.3 Hz, H-1).

Example 17

(17Z)-3-Hydroxy-19-Norpregna-1,3,5(10),17(20)-tetraene, 3-O-dimethylthexylsilyl ether Potassium tert-butoxide (325 mg, 2.90 mmol) was added to a solution of ethyltriphenylphosphonium bromide (1.08 g, 2.90 mmol) in dry DMSO (6.0 ml) under N₂. After stirring for 20 min the temperature was raised to 75° C. and a solution of 3-hydroxy-17-keto-estra-1,3,5(10)-triene, 3-O-dimethylthexylsilyl ether (1.00 g, 2.42 mmol) in dry THF (4.0 ml) was added. The reaction mixture was stirred at 75° C. for 2.5 h. After cooling the reaction mixture was partitioned in Et₂O/H₂O and the organic phase was washed with H₂O, dried over Na₂SO₄, and concentrated at reduced pressure. The residue was purified by column chromatography (heptane) to give the title compound as an approximately 1:1 epimeric mixture (85 mg, 28%).

$R_f$ (heptane)=0.2

$^1$H NMR (CDCl$_3$) δ 0.22 (s, 6H, —Si(CH$_3$)$_2$—), 0.91 (s, 3H, H-18), 0.94 (s, 6H, thexyl), 0.94 (d, 6H, J=6.8 Hz, thexyl), 1.7 (m, 3H, H-21), 6.54 (d, 1H, J=2.6 Hz, H-4), 6.61 (dd, 1H, J=2.6 Hz, 8.7 Hz, H-2), 7.13 (d, 1H, J=8.7 Hz, H-1).

Example 18
(17E)-3,16α-Dihydroxy-19-Norpregna-1,3,5(10),17(20)-tetraene, 3-O-dimethylthexylsilyl ether Prepared from (17Z)-3-hydroxy-19-norpregna-1,3,5(10),17(20)-tetraene, 3-O-dimethylthexylsilyl ether according to procedure A.

Yield: 140 mg (51%)

$R_f$ (10:1)=0.07

$^1$H NMR (CDCl$_3$) δ 0.22 (s, 6H, —Si(CH$_3$)$_2$—), 0.92 (s, 3H, H-18), 0.94 (s, 6H, thexyl), 0.94 (d, 6H, J=6.8 Hz, thexyl), 1.78 (d, 3H, J=7 Hz, H-21), 4.48 (s, 1H, H-16), 6.56 (d, 1H, J=2.2 Hz, H-4), 6.62 (dd, 1H, J=2.2 Hz, 8.6 Hz, H-2), 7.12 (d, 1H, J=8.6 Hz, H-1).

Example 19
(17E)-3,16α-Dihydroxy-19-Norpregna-1,3,5(10),17(20)-tetraene

Prepared from (17E)-3,16α-dihydroxy-19-norpregna-1,3,5(10),17(20)-tetraene, 3-O-dimethyl-thexylsilyl ether according to procedure B.

Yield: 30 mg (84%)

$R_f$ (1:1)=0.39 mp 225–31 °C.

MS(FAB): m/z=298

$^1$H NMR (CDCl$_3$) δ 0.92 (s, 3H, H-18), 1.78 (d, 3H, J=7 Hz, H-21), 4.48 (s, 1H, H-16), 6.57 (d, 1H, J=2.6 Hz, H-4), 6.63 (dd, 1H, J=2.6 Hz, 8.5 Hz, H-2), 7.16 (d, 1H, J=8.5 Hz, H-1).

Example 20
Etyl (17E)-3-Hydroxy-19-Norpregna-1,3,5(10),17(20)-tetraene-21-oate, 3-O-dimethylthexylsilyl ether Triethyl phosphonoacetate (3.00 mL, 15.0 mnol) was added dropwise to a slurry of NaH (480 mg, ca 60% in oil, 12 mmol) in dry dimethoxyethane (DME, 30 ml) under N$_2$. After 10 min stirring, a solution of 3-hydroxy-17-keto-estra-1,3,5(10)-triene, 3-dimethylthexylsilyl ether (2.064 g, 5.00 mmol) in dry DME (15 ml) was added. The temperature was raised to 90° C. and the reaction mixture was stirred over night. After cooling heptane (20 ml) was added and most of the DME was removed by evaporation at reduced pressure. The residue was partitioned in Et$_2$O/H$_2$O and the organic phase was then washed with brine, dried over Na$_2$SO$_4$, and concentrated at reduced pressure. The residue was purified by column chromatography (heptane-EtOAc, 50:1, 20:1) to give the title compound as a white solid (1.494 mg, 62%).

$R_f$ (20:1)=0.30;

$^1$H NMR (CDCl$_3$) δ 0.22 (s, 6H, —Si(CH$_3$)$_2$—), 0.86 (s, 3H, H-18), 0.94 (s, 6H, thexyl), 0.94 (d, 6H, J=6.8 Hz, thexyl), 1.29 (t, 3H, J=7.1 Hz, Et), 4.16 (q, 2H, J=7.1 Hz, Et), 5.59 (dd, 1H, J=2.4 Hz, 2.4 Hz, H-20), 6.55 (d, 1H, J=2.7 Hz, H-4), 6.61 (dd, 1H, J=2.7 Hz, 8.5 Hz, H-2), 7.12 (d, 1H, J=8.5 Hz, H-1).

Example 21
(17E)-3,21-Dihydroxy-19-Norpregna-1,3,5(10),17(20)-tetraene, 3-O-dimethylthexylsilyl ether Lithium triethylborohydride (6.0 mL, 1 M in THF, 6.0 mmol) was added to a solution of etyl (17E)-3-hydroxy-19-norpregna-1,3,5(10),17(20)-tetraene-21-oate, 3-O-dimethylthexylsilyl ether (1.320 g, 2.73 mmol) in dry THF (6.0 mL) at 0° C. under N$_2$. The reaction mixture was stirred for another 10 min and was then partitioned in Et$_2$O/brine and acidified with 1 M HCl (ca 10 mL). The organic phase was washed with brine, dried over Na$_2$SO$_4$, and concentrated at reduced pressure. The residue was purified by column chromatography (heptane-EtOAc, 5:1, 3:1) to give the title compound as a white solid (1.048 mg, 87%).

$R_f$ (3:1)=0.27

$^1$H NMR (CDCl$_3$) δ 0.22 (s, 6H, —Si(CH$_3$)$_2$—), 0.81 (s, 3H, H-18), 0.94 (s, 6H, thexyl), 0.94 (d, 6H, J=6.8 Hz, thexyl), 4.14 (m, 2H, H-21), 5.29 (m, 1H, H-20), 6.54 (d, 1H, J=2.4 Hz, H-4), 6.61 (dd, 1H, J=2.4 Hz, 8.1 Hz, H-2), 7.13 (d, 1H, J=8.1 Hz, H-1).

Example 22
(17E)-3-Hydroxy-19-Norpregna-1,3,5(10),17(20)-tetraene, 3-O-dimethylthexylsilyl ether Methanesulfonic anhydride (52 mg, 0.3 mmol) was added to a solution of (17E)-3,21-dihydroxy-19-norpregna-1,3,5(10),17(20)-tetraene, 3-O-dimethylthexylsilyl ether (74 mg, 0.17 mmol) and 2,6-lutidine (46 μL, 0.4 mmol) in dry THF (0.5 mL) under N$_2$. After 5 min stirring, lithium triethylborohydride (500 μL, 1 M in THF, 0.50 mmol) was added. The reaction mixture was stirred for another 10 min and was then partitioned in Et$_2$O/brine and acidified with 1 M HCl (ca 5 mL). The organic phase was washed with brine, NaHCO$_3$ (sat.) and brine again, dried over Na$_2$SO$_4$, and concentrated at reduced pressure. The residue was purified by column chromatography (heptane-EtOAc, 50:1) to give the title compound as an oil (40 mg, 56%).

$R_f$ (50:1)=0.30

$^1$H NMR (CDCl$_3$) δ 0.21 (s, 6H, —Si(CH$_3$)$_2$—), 0.77 (s, 3H, H-18), 0.94 (s, 6H, thexyl), 0.94 (d, 6H, J=7.1 Hz, thexyl), 1.56 (ddd, 3H, J=6.6 Hz, 1.5 Hz, 1.5 Hz, H-21), 5.08 (m, 1H, H- 20), 6.54 (d, 1H, J=2.7 Hz, H-4), 6.60 (dd, 1H, J=2.7 Hz, 8.3 Hz, H-2), 7.14 (d, 1H, J=8.3 Hz, H-1).

Example 23
(17Z)-3,16α-Dihydroxy-19-Norpregna-1,3,5(10),17(20)-tetraene, 3-O-dimethylthexylsilyl ether Prepared from (17E)-3-hydroxy-19-norpregna-1,3,5(10), 17(20)-tetraene, 3-O-dimethylthexylsilyl ether according to procedure A.

Yield: 25 mg (45%)

$R_f$ (5:1)=0.29

$^1$H NMR (CDCl$_3$) δ 0.21 (s, 6H, —Si(CH$_3$)$_2$—), 0.77 (s, 3H, H-18), 0.94 (s, 6H, thexyl), 0.94 (d, 6H, J=7 Hz, thexyl), 1.81 (d, 3H, J=7 Hz, H-21), 4.85 (m, 1H, H-16), 5.37 (dq, 1H, J=2 Hz, 7 Hz, H-20), 6.55 (d, 1H, J=2.7 Hz, H-4), 6.61 (dd, 1H, J=2.7 Hz, 8.2 Hz, H-2), 7.12 (d, 1H, J=8.2 Hz, H-1).

Example 24
(17Z)-3-Hydroxy-16-keto-19-Norpregna-1,3,5(10),17(20)-tetraene, 3-O-dimethylthexylsilyl ether The reaction according to Example 23 also provided the compound of this Example.

Yield: 20 mg (36%)

$R_f$ (10:1)=0.19

$^1$H NMR (CDCl$_3$) δ 0.22 (s, 6H, —Si(CH$_3$)$_2$—), 0.94 (s, 6H, thexyl), 0.94 (d, 6H, J=6.8 Hz, thexyl), 1.06 (s, 3H, H-18), 1.89 (d, 3H, J=7.6 Hz, H-21), 6.54 (q, 1H, J=7.6 Hz, H-20), 6.56 (d, 1H, J=2.7 Hz, H-4), 6.63 (dd, 1H, J=2.7 Hz, 8.5 Hz, H-2), 7.12 (d, 1H, J=8.5 Hz, H-1).

Example 25
(17Z)-3,16α-Dihydroxy-19-Norpregna-1,3,5(10),17(20)-tetraene

Prepared from (17Z)-3,16α-dihydroxy-19-norpregna-1,3,5(10),17(20)-tetraene, 3-dimethyl-thexylsilyl ether according to procedure B.

Yield: 11 mg (82%)
R$_f$ (2:1)=0.26
mp 228–32° C.
MS-FAB: m/z=298 (M$^+$)
$^1$H NMR (CDCl$_3$) δ 0.77 (s, 3H, H-18), 1.81 (d, 3H, J=6.8 Hz, H-21), 4.57 (s, 1H, 3-OH), 4.85 (m, 1H, H-16), 5.38 (dq, 1H, J=1.7 Hz, 6.8 Hz, H-20), 6.57 (d, 1H, J=2.7 Hz, H-4), 6.63 (dd, 1H, J=2.7 Hz, 8.5 Hz, H-2), 7.16 (d, 1H, J=8.5 Hz, H-1).

Example 26

3,16α,17β-Trihydroxy-estra-1,3,5(10)-triene, 3,16α-Bis(dimethylthexylsilyl ether)

Dimethylthexylchlorosilane (1.47 ml, 7.49 mmol) was added to a solution of 3,16α,17β-trihydroxy-estra-1,3,5(10)-triene (estriol, 1.00 g, 3.47 mmol) and imidazole (1.02 g, 15.0 mmol) in dry DMF (2.0 ml). The reaction mixture was stirred for 30 min and the raw product was then purified directly by column chromatography (heptane-EtOAc, 10:1) to give the title compound as an oil which crystallized on standing (1.95 g, 98%).
R$_f$ (10:1)=0.22
$^1$H NMR (CDCl$_3$) δ 0.11 (s, 3H, —SiMe$_2$—), 0.13 (s, 3H, —SiMe$_2$—), 0.21 (s, 6H, —SiMe$_2$—), 0.78 (s, 3H, H-18), 0.86 (s, 6H, thexyl), 0.90 (d, 6H, J=6.8 Hz, thexyl), 0.94 (s, 6H, thexyl), 0.94 (d, 6H, J=6.8 Hz, thexyl), 3.56 (t, 1H, J=5.4 Hz, H-17), 4.07 (m, 1H, H-16), 6.54 (d, 1H, J=2.7Hz, H-4), 6.60 (dd, 1H, J=2.7 Hz, 8.3Hz, H-2), 7.11 (d, 1H, J=8.3 Hz, H-1).

Example 27

3,16α-Dihydroxy-17-keto-estra-1,3,5(10)-triene, 3,16α-Bis(dimethyl-thexylsilyl ether)

N-methylmorphonlin (300 mg, 2.22 mmol) and tetrapropylammonium perruthenate (TPAP, 40 mg, 0.11 mmol) were added to a solution of 3,16α,17β-trihydroxy-estra-1,3,5(10)-triene, 3,16α-bis(dimethyl-thexylsilyl ether) (790 mg, 1.38 mmol) in CH$_2$Cl$_2$ (3.0 ml). The solution was stirred for 6 h at room temperature and was then concentrated at reduced pressure. The residue was purified by column chromatography (heptane-EtOAc, 50:1, 20:1) to give the title compound as an oil (600 mg, 76%).
R$_f$ (20:1)=0.33
$^1$H NMR (CDCl$_3$) δ 0.15 (s, 3H, —SiMe$_2$—), 0.18 (s, 3H, —SiMe$_2$—), 0.22 (s, 6H, —SiMe$_2$—), 0.86 (s, 6H, thexyl), 0.88 (d, 3H, J=6.8 Hz, thexyl), 0.89 (d, 3H, J=6.8 Hz, thexyl), 0.93 (s, 3H, H-18), 0.94 (s, 6H, thexyl), 0.94 (d, 6H, J=6.8 Hz, thexyl), 4.36 (d, 1H, J=7.5 Hz, H-16), 6.55 (d, 1H, J=2.7 Hz, H-4), 6.61 (dd, 1H, J=2.7 Hz, 8.3 Hz, H-2), 7.11 (d, 1H, J=8.3 Hz, H-1).

Example 28

17-Difluoromethylene-3,16α-dihydroxy-estra-1,3,5(10)-triene, 3,16α-Bis(dimethylthexylsilyl ether)

Lithium diisopropylamide (750 μl, 1.5 M THF-complex in hexane, 1.12 mmol) was added to a solution of F$_2$CHPO(OEt)$_2$ (215 mg, 1.14 mmol) in dry THF (1.0 ml) under N$_2$ at −78° C. After 5 min stirring, a solution of 3,16α-dihydroxy-17-keto-estra-1,3,5(10)-triene, 3,16α-bis(dimethyl-thexylsilyl ether) (173 mg, 0.30 mmol) in dry THF was added and the reaction mixture was stirred at −78° C. for 1 h, then at 60° C. over night. After cooling, the reaction mixture was diluted with Et$_2$O (100 ml) and acidified with 1M HCl. The organic phase was washed with brine, dried over Na$_2$SO$_4$ and concentrated at reduced pressure. The residue (268 mg of a brown oil) was purified by column chromatography (heptane, then heptane-EtOAc, 50:1, then 20:1) to give the title compound as an oil (102 mg, 56%).

R$_f$ (50:1)=0.33
$^1$H-NMR (CDCl$_3$) δ 0.11 (s, 6H, —SiMe$_2$—), 0.21 (s, 6H, —SiMe$_2$—), 0.82 (s, 6H, thexyl), 0.87 (2d, 6H, J=6 Hz, thexyl), 0.88 (s, 3H, H-18), 0.94 (s, 6H, thexyl), 0.94 (d, 6H, J=6.9 Hz, thexyl), 4.77 (dd, 1H, J=1.6 Hz, 5.2 Hz, H-16), 6.54 (d, 1H, J=2.7 Hz, H-4), 6.61 (dd, 1H, J=2.7 Hz, 8.4 Hz, H-2), 7.11 (d, 1H, J=8.4 Hz, H-1).

Example 29

17-Difluoromethylene-3,16α-dihydroxy-estra-1,3,5(10)-triene

NBu$_4$F.(H$_2$O)$_3$ (200 mg, 0.63 mmol) was added to a solution of 17-difluoromethylene-3,16α-dihydroxy-estra-1,3,5(10)-triene, 3,16α-bis(dimethyl-thexylsilyl ether) (100 mg, 0.165 mmol) in dry THF (1.0 ml). The reaction mixture was stirred for 2 h at 50° C. and was then quenched by adding AcOH (100 μl). Concentration at reduced pressure was followed by purification by column chromatography (heptane-EtOAc, 3:1, 2:1) to give the title compound as a white solid (19 mg, 36%):
R$_f$ (2:1)=0.28
mp 225–27° C.
MS-FAB: m/z=320 (M$^+$)
$^1$H NMR (CDCl$_3$) δ 0.91 (s, 3H, H-18), 4.52 (s, 1H, 3-OH), 4.89 (m, 1H, H-16), 6.57 (d, 1H, J=2.7 Hz, H-4), 6.63 (dd, 1H, J=2.7 Hz, 8.5 Hz, H-2), 7.15 (d, 1H, J=8.5 Hz, H-1).

3-O-Alkylether derivatives

General Procedure for 3-O-alkylation of 3,16α-dihydroxy-17-methylene-estra-1,3,5(10)-triene 3,16α-Dihydroxy-17-methylene-estra-1,3,5(10)-triene (0.32 mmol), alkyl iodide (0.42 mmol), Cs$_2$CO$_3$ (0.70 mmol) and dry DMF (0.5–1.0 mL) under dry nitrogen were stirred over night at 40–80° C. The volatiles were evaporated at reduced pressure and the residue was partitioned between saturated NH$_4$Cl and EtOAc (2×10 mL). The organic phases were combined, washed with brine, dried over anhydrous Na$_2$SO$_4$, filtered and concentrated at reduced pressure. The residue was purified by column chromatography on silica (heptane-EtOAc, 5:1) to give the 3-O-alkylether.

The following 3-O-alkyl ethers were prepared:

Example 30

3,16α-Dihydroxy-17-methylene-estra-1,3,5(10)-triene, 3-O-Cyclopentyl ether
Yield: 59%; colourless crystalline solid
R$_f$ (3:1)=0.25
MS(EI) m/z 352 (M$^+$)
$^1$H NMR (CDCl$_3$) δ 0.82 (s, 3H, H-18), 4.67–4.75 (m, 2H), 4.92 (d, 1H, J=1.8 Hz, =CH$_2$), 5.08 (d, 1H, J=1.5 Hz, =CH$_2$), 6.60 (d, 1H, J=2.6 Hz, H-4), 6.67 (dd, 1H, J=8.4 Hz, J=2.6 Hz, H-2), 7.18 (d, 1H, J=8.4 Hz, H-1).

Example 31

3,16α-Dihydroxy-17-methylene-estra-1,3,5(10)-triene, 3-O-methyl ether
Yield: 49%; colourless crystalline solid
R$_f$ (2:1)=0.24
MS(EI) m/z 298 (M$^+$)
$^1$H NMR (CDCl$_3$) δ 0.83 (s, 3H, H-18), 3.78 (s, 3H, —OCH$_3$), 4.69–4.75 (m, 1H, H-16), 4.93 (d, 1H, J=2.4 Hz, =CH$_2$), 5.09 (d, 1H, J=1.8 Hz, =CH$_2$), 6.64 (d, 1H, J=2.7 Hz, H-4), 6.72 (dd, 1H, J=8.4 Hz, J=2.7 Hz, H-2), 7.22 (d, 1H, J=8.7 Hz, H-1).

Ester and carbonic-acid ester derivatives

General Procedure for 3-O-Monoesterification of 3,16α-Dihydroxy-17-methylene-estra-1,3,5(10)-triene:

An acid chloride or chloroformate ester (0.36 mmol) in dry dioxane (0.35 mL) was added during 15 minutes to a rapidly stirred mixture of 3,16α-dihydroxy-17-methylene-estra-1,3,5(10)-triene (0.090 g, 0.32 mmol), ground NaOH (0.035 g), tetrabutylammonium hydrogen sulfate (2–4 mg) and dioxane (0.80 mL). After stirring at room temperature for 10–30 minutes saturated $NH_4Cl$ (2 mL), water (0.5 mL) and EtOAc (10 mL) were added. The organic phase was separated, washed with brine, dried over anhydrous $Na_2SO_4$, filtered and concentrated at reduced pressure. The residue was purified by column chromatography on silica (with the eluent indicated below) to give the title compound.

Yields: 40–60%.

The following 3-O-monoesters were prepared:

Example 32
3,16α-Dihydroxy-17-methylene-estra-1,3,5(10)-triene, 3-acetate $R_f$ (1:1)=0.31

$^1H$ NMR ($CDCl_3$) δ 0.83 (s, 3H, H-18), 2.28 (s, 3H, Ac), 4.72 (m, 1H, H-16), 4.93 (d, 1H, J=2.2 Hz, =$CH_2$), 5.09 (d, 1H, J=1.7 Hz, =$CH_2$), 6.80 (d, 1H, J=2.4 Hz, H-4), 6.85 (dd, 1H, J=2.4 Hz, 8.6 Hz, H-2), 7.29 (d, 1H, J=8.6 Hz, H-1).

Example 33
3,16α-Dihydroxy-17-methylene-estra-1,3,5(10)-triene, 3-Benzoate $R_f$ (3:1)=0.20

$^1H$ NMR ($CDCl_3$) δ 0.85 (s, 3H, H-18), 4.73 (m, 1H, H-16), 4.94 (d, 1H, J=2.0 Hz, =$CH_2$), 5.10 (d, 1H, J=1.7 Hz, =$CH_2$), 6.93 (d, 1H, J=2.4 Hz, H-4), 6.98 (dd, 1H, J=2.4 Hz, 8.3 Hz, H-2), 7.35 (d, 1H, J=8.3 Hz, H-1), 7.51 (m, 2H, Bz), 7.63 (m, 1H, Bz), 8.20 (m, 2H, Bz).

Example 34
3,16α-Dihydroxy-17-methylene-estra-1,3,5(10)-triene, 3-Hexanoate $R_f$ (1:1)=0.37

$^1H$ NMR ($CDCl_3$) δ 0.84 (s, 3H, H-18), 0.90–0.98 (m, 3H), 2.54 (t, J=7.5 Hz, 2H), 4.69–4.76 (m, 1H, H-16), 4.91 (d, 1H, J=2.4 Hz, =$CH_2$), 5.10 (d, 1H, J=1.8 Hz, =$CH_2$), 6.80 (d, 1H, J=2.4 Hz, H-4), 6.85 (dd, 1H, J=8.4 Hz, J=2.4 Hz, H-2), 7.30 (d, 1H, J=8.4 Hz, H-1).

Example 35
3,16α-Dihydroxy-17-methylene-estra-1,3,5(10)-triene, 3-Octadecanoate $R_f$ (2:1)=0.29

$^1H$ NMR ($CDCl_3$) δ 0.83 (s, 3H, H-18), 0.85–0.92 (m, 3H), 2.53 (t, J=7.5 Hz, 2H), 4.68–4.76 (m, 1H, H-16), 4.92–4.94 ("d", 1H, =$CH_2$), 5.07–5.11 ("d", 1H, =$CH_2$), 6.77–6.80 (m, 1H, H-4), 6.81–6.86 (m, 1H, H-2) and 7.28 (d, 1H, J=9.0 Hz, H-1).

Example 36
3,16α-Dihydroxy-17-methylene-estra-1,3,5(10)-triene, 3-methylcarbonate $R_f$ (2:1)=0.19

$^1H$ NMR ($CDCl_3$) δ 0.83 (s, 3H, H-18), 3.89 (s, 3H, —$OCH_3$), 4.68–4.75 (m, 1H, H-16), 4.93 (d, 1H, J=2.1 Hz, =$CH_2$), 5.09 (d, 1H, J=1.8 Hz, =$CH_2$), 6.88 (d, 1H, J=2.4 Hz, H-4), 6.93 (dd, 1H, J=8.4 Hz, J=2.4 Hz, H-2), 7.29 (d, 1H, J=8.4 Hz, H-1).

Example 37
3,16α-Dihydroxy-17-methylene-estra-1,3,5(10)-triene, 3-Butylcarbonate $R_f$ (1:1)=0.45

$^1H$ NMR ($CDCl_3$) δ 0.83 (s, 3H, H-18), 0.97 (t, J=7.2 Hz, 3H), 4.24 (t, J=6.6 Hz, 2H), 4.68–4.75 (m, 1H, H-16), 4.92 (d, 1H, J=1.8 Hz, =$CH_2$), 5.08 (d, 1H, J=1.2 Hz, =$CH_2$), 6.89 (d, 1H, J=2.4 Hz, H-4), 6.94 (dd, 1H, J=8.4 Hz, J=2.4 Hz, H-2) and 7.29 (d, 1H, J=8.1 Hz, H-1).

Example 38
3,16α-Dihydroxy-17-methylene-estra-1,3,5(10)-triene, 3-Benzylcarbonate $R_f$ (2:1)=0.21

$^1H$ NMR ($CDCl_3$) δ 0.82 (s, 3H, H-18), 4.68–4.74 (m, 1H, H-16), 4.92 (d, 1H, J=1.8 Hz, =$CH_2$), 5.08 (d, 1H, J=1.5 Hz, =$CH_2$), 5.25 (s, 2H, $OCH_2Ph$), 6.88 (d, 1H, J=2.4 Hz, H-4), 6.94 (dd, 1H, J=8.7 Hz, J=2.7 Hz, H-2), 7.29 (d, 1H, J=8.4 Hz, H-1), 7.34–7.46 (m, 5H, $C_6H_5$—).

General Procedure for 16α-O-Monoesterification of 3,16α-dihydroxy-17-methylene-estra-1,3,5(10)-triene:

An ester anhydride or ester chloride (1.1 mmol) was added to a solution of 3,16α-dihydroxy-D17-methylene-estra-1,3,5(10)-triene, 3-O-dimethylthexylsilyl ether (1.0 mmol) and N,N-dimethylaminopyridine (1.5 mmol) in $CH_2Cl_2$ (1.5 mL). The reaction mixture was stuffed for 1–4 h and was then concentrated at reduced pressure. The residue was filtered through a short silica gel column (heptane-EtOAc mixtures as eluents). The filtrate was concentrated at reduced pressure and the residue was treated according to Procedure B.

Yields: 60–80%.

The following 16α-O-monoester derivatives were prepared:

Example 39
3,16α-Dihydroxy-17-methylene-estra-1,3,5(10)-triene, 16α-Acetate $R_f$ (5:1)=0.17

$^1H$ NMR ($CDCl_3$) δ 0.85 (s, 3H, H-18), 2.11 (s, 3H, Ac), 4.64 (s, 1H, phenol), 4.94 (d, 1H, J=2.0 Hz, =$CH_2$), 4.97 (d, 1H, J=1.7 Hz, =$CH_2$), 5.72 (broad d, 1H, J=7.8 Hz, H-16), 6.57 (d, 1H, J=2.7 Hz, H-4), 6.63 (dd, 1H, J=2.7 Hz, 8.6 Hz, H-2), 7.16 (d, 1H, J=8.6 Hz, H-1).

Example 40
3,16α-Dihydroxy-17-methylene-estra-1,3,5(10)-triene, 16α-Hexanoate $R_f$ (5:1)=0.22

$^1H$ NMR ($CDCl_3$) δ 0.84 (s, 3H, H-18), 0.90 (t, 3H, J=7 Hz), 2.35 (t, 2H, J=7.5 Hz), 4.93 (d, 1H, J=2.1, Hz, =$CH_2$), 4.95 (d, 1H, J=1.8 Hz, =$CH_2$), 5.73 (d, 1H, J=6.9 Hz, H-16), 6.57 (d, 1H, J=2.7 Hz, H-4), 6.65 (dd, 1H, J=2.7 Hz, 8.4 Hz, H-2), 7.15 (d, 1H, J=8.4 Hz, H-1).

Example 41
3,16α-Dihydroxy-17-methylene-estra-1,3,5(10)-triene, 16α-Octadecanoate $R_f$ (5:1)=0.23

$^1H$ NMR ($CDCl_3$) δ 0.86 (s, 3H, H-18), 0.88 (t, 3H, J=7 Hz), 2.34 (t, 2H, J=7.5 Hz), 4.55 (s, 1H, phenol), 4.93 (d, 1H, J=2.3, Hz, =$CH_2$), 4.95 (d, 1H, J=1.7 Hz, =$CH_2$), 5.73 (broad d, 1H, J=6.3 Hz, H-16), 6.56 (d, 1H, J=2.9 Hz, H-4), 6.64 (dd, 1H, J=2.9 Hz, 8.2 Hz, H-2), 7.16 (d, 1H, J=8.2 Hz, H-1).

Example 42
3,16α-Dihydroxy-17-methylene-estra-1,3,5(10)-triene, 16α-Benzoate $R_f$ (5:1)=0.12

$^1H$ NMR ($CDCl_3$) δ 0.92 (s, 3H, H-18), 4.53 (s, 1H, phenol), 4.99 (d, 1H, J=2.1, Hz, =$CH_2$), 5.07 (d, 1H, J=1.8 Hz, =$CH_2$), 5.95 (broad d, 1H, J=6.6 Hz, H-16), 6.57 (d, 1H, J=2.7 Hz, H-4), 6.64 (dd, 1H, J=2.7 Hz, 8.7 Hz, H-2), 7.18 (d, 1H, J=8.7 Hz, H-1), 7.45 (t, 2H, J=7.4 Hz, Ph), 7.57 (m, 1H, Ph), 8.08 (d, 2H, J=7.4 Hz, Ph).

Example 43

3,16α-Dihydroxy-17-methylene-estra-1,3,5(10)-triene, 16α-methylcarbonate $R_f$ (3:1)=0.27

$^1$H NMR (CDCl$_3$) δ 0.85 (s, 3H, H-18), 3.81 (s, 3H, OMe), 4.76 (s, 1H, phenol), 5.00 (d, 1H, J=2.2 Hz, =CH$_2$), 5.05 (d, 1H, J=1.7 Hz, =CH$_2$), 5.59 (m, 1H, H-16), 6.57 (d, 1H, J=2.7 Hz, H-4), 6.63 (dd, 1H, J=2.7 Hz, 8.3 Hz, H-2), 7.16 (d, 1H, J=8.3 Hz, H-1).

Example 44

3,16α-Dihydroxy-17-methylene-estra-1,3,5(10)-triene, 16α-n-Butylcarbonate $R_f$ (5:1)=0.16

$^1$H NMR (CDCl$_3$) δ 0.85 (s, 1H, H-18), 0.94 (t, J=7.5 Hz, 3H), 4.17 (t, 2H, J=6.6 Hz), 4.99 (s, 1H, =CH$_2$), 5.10 (s, 1H, =CH$_2$), 5.60 (m, 1H, H-16), 6.57 (d, 1H, J=2.7 Hz, H-4), 6.62 (dd, 1H, J=2.7 Hz, 8.5 Hz, H-2), 7.16 (d, 1H, J=8.5 Hz, H-1).

Example 45

3,16α-Dihydroxy-17-methylene-estra-1,3,5(10)-triene, 16α-Benzylcarbonate $R_f$ (5:1)=0.14

$^1$H NMR (CDCl$_3$) δ 0.85 (s, 1H, H-18), 4.98 (d, 1H, J=1.8 Hz, =CH$_2$), 5.09 (d, 1H, J=1.5 Hz, =CH$_2$), 5.19 (s, 2H, benzyl), 5.62 (m, 1H, H-16), 6.56 (d, 1H, J=2.7 Hz, H-4), 6.63 (dd, 1H, J=2.7 Hz, 8.4 Hz, H-2), 7.15 (d, 1H, J=8.4 Hz, H-1), 7.33–7.42 (m, 5H, Ph).

General Procedure for 3-O,16α-O-diesterification of 3,16α-dihydroxy-17-methylene-estra-1,3,5(10)-triene:

An ester anhydride or ester chloride (3.0 mmol) was added to a solution of 3,16α-dihydroxy-17-methylene-estra-1,3,5(10)-triene (1.0 mmol) and N,N-dimethylaminopyridine (4.0 mmol) in CH$_2$Cl$_2$ (1.5 nmL). The reaction mixture was stirred for 1–3 h and was then concentrated at reduced pressure. The residue was purified by column chromatography (heptane-EtOAc) to give the 3,16α-diester derivatives.

Yields ca 70–80%.

The following 3-O,16α-O-diesters were prepared:

Example 46

3,16α-Dihydroxy-17-methylene-estra-1,3,5(10)-triene, 3,16α-diacetate $R_f$ (10:1)=0.33

$^1$H NMR (CDCl$_3$) δ 0.85 (s, 3H, H-18), 2.10 (s, 3H, Ac), 2.28 (s, 3H, Ac), 4.95 (d, 1H, J=2.0 Hz, =CH$_2$), 4.98 (d, 1H, J=1.5 Hz, =CH$_2$), 5.73 (broad d, 1H, J=7.8 Hz, H-16), 6.80 (d, 1H, J=2.4 Hz, H-4), 6.85 (dd, 1H, J=2.4 Hz, 8.6 Hz, H-2), 7.29 (d, 1H, J=8.6 Hz, H-1).

Example 47

3,16α-Dihydroxy-17-methylene-estra-1,3,5(10)-triene, 3,16α-dihexanoate $R_f$ (5:1)=0.61

$^1$H NMR (CDCl$_3$) δ 0.86 (s, 1H, H-18), 0.91 (m, 6H), 2.34 (t, 2H, J=7.5 Hz), 2.53 (t, 2H, J=7.5 Hz), 4.93 (d, 1H, J=2.2 Hz, =CH$_2$), 4.95 (d, 1H, J=1.7 Hz, =CH$_2$), 5.73 (broad d, 1H, J=6.9 Hz, H-16), 6.78 (d, 1H, J=2.5 Hz, H-4), 6.84 (dd, 1H, J=2.5 Hz, 8.4 Hz, H-2), 7.29 (d, 1H, J=8.4 Hz, H-1).

Example 48

3,16α-Dihydroxy-17-methylene-estra-1,3,5(10)-triene, 3,16α-dihexadecanoate $R_f$ (20:1)=0.27

$^1$H NMR (CDCl$_3$) δ 0.84–0.92 (m, 9H), 2.34 (t, 2H, J=7.5 Hz), 2.53 (t, 2H, J=7.5 Hz), 4.93 (d, 1H, J=2.2 Hz, =CH$_2$), 4.95 (d, 1H, J=1.7 Hz, =CH$_2$), 5.73 (broad d, 1H, J=7.6 Hz, H-16), 6.78 (d, 1H, J=2.4 Hz, H-4), 6.84 (dd, 1H, J=2.4 Hz, 8.5 Hz, H-2), 7.29 (d, 1H, J=8.5 Hz, H-1).

Example 49

3,16α-Dihydroxy-17-methylene-estra-1,3,5(10)-triene, 3,16α-dibenzoate $R_f$ (5:1)=0.34

$^1$H NMR (CDCl$_3$) δ 0.93 (s, 1H, H-18), 5.00 (d, 1H, J=2 Hz, =CH$_2$), 5.08 (d, 1H, J=2 Hz, =CH$_2$), 5.96 (d, 1H, J=7.5 Hz, H-16), 6.94 (d, 1H, J=2.4 Hz, H-4), 6.99 (dd, 1H, J=2.4 Hz, 8.7 Hz, H-2), 7.46 (d, 1H, J=8.7 Hz, H-1), 7.30–7.70 (m, 4H), 8.07–8.22 (m, 6H).

Example 50

3,16α-Dihydroxy-17-methylene-estra-1,3,5(10)-triene, 3,16α-di(methylcarbonate)

$R_f$ (5:1)=0.24

$^1$H NMR (CDCl$_3$) δ 0.85 (s, 1H, H-18), 3.81 (s, 3H, —OCH$_3$), 3.89 (s, 3H, —OCH$_3$), 5.03 (d, 1H, J=2.2 Hz, =CH$_2$), 5.10 (d, 1H, J=1.7 Hz, =CH$_2$), 5.59 (m, 1H, H-16), 6.89 (d, 1H, J=2.4 Hz, H-4), 6.93 (dd, 1H, J=2.4 Hz, 8.4 Hz, H-2), 7.29 (d, 1H, J=8.4 Hz, H-1).

Example 51

3,16α-Dihydroxy-17-methylene-estra-1,3,5(10)-triene, 3,16α-di(n-butylcarbonate)

$R_f$ (5:1)=0.50

$^1$H NMR (CDCl$_3$) δ 0.85 (s, 1H, H-18), 0.96 (m, 6H), 4.17 (t, 2H, J=6.8 Hz), 4.24 (t, 2H, J=6.8 Hz), 4.99 (d, 1H, J=2.1 Hz, =CH$_2$), 5.11 (d, 1H, J=1.8 Hz, =CH$_2$), 5.60 (m, 1H, H-16), 6.89 (d, 1H, J=2.4 Hz, H-4), 6.93 (dd, 1H, J=2.4 Hz, 8.5 Hz, H-2), 7.28 (d, 1H, J=8.5 Hz, H-1).

Example 52

3,16α-Dihydroxy-17-methylene-estra-1,3,5(10)-triene, 3,16α-di(benzylcarbonate)

$R_f$ (5:1)=0.23

$^1$H NMR (CDCl$_3$) δ 0.84 (s, 1H, H-18), 4.99 (d, 1H, J=2 Hz, =CH$_2$), 5.10 (d, 1H, J=2 Hz, =CH$_2$), 5.19, 5.26 (2s, 4H, benzyl), 5.62 (m, 1H, H-16), 6.88 (d, 1H, J=2.4 Hz, H-4), 6.94 (dd, 1H, J=2.4 Hz, 8.4 Hz, H-2), 7.26–7.43 (m, 11H, H-1, Ph).

Example 53

17-(1',2'-Ethylene)-3-hydroxy-16-keto-estra-1,3,5(10)-trienene, 3-dimethyl-thexylsilyl ether NaH (55–65% in oil, 120 mg, 3.0 mmol) was washed under N$_2$ three times with dry n-hexane and dried at reduced pressure. Dry DMSO (3.0 mL) was then added followed by finely ground and vacuum-dried trimethylsulfoxonium iodide (662 mg, 3.0 mmol). The mixture was stirred under nitrogen until the hydrogen gas evolution ceased and the solution became clear (within 20 min), then transferred dropwise to a stirred solution of 3-hydroxy-16-keto-17-metylene-estra-1,3,5(10)-trienene, 3-dimethyl-thexylsilyl ether (1.27 g, 3.0 mmol) in dry DMSO (2.0 mL) and dry THF (2.0 mL. After stirring for 2 h at room temperature EtOAc (20 mL) was added and the solution was washed five times with 5% aqueous NaCl. Then the organic phase was washed with brine, dried over anhydrous Na$_2$SO$_4$, filtered and concentrated at reduced pressure. The residual yellow oil was purified by column chromatography (toluene as eluent) to give the title compound (230 mg, 18%) as a colourless oil, which solidified upon cooling.

TLC: $R_f$(toluene)=0.21

MS(EI) m/z 438 (M$^+$)

$^1$H NMR (CDCl$_3$) δ 0.23 (s, 6H), 0.65–0.70 (m, 1H), 0.76–0.81 (m, 1H), 0.95 (s, 3H), 0.96 (s, 6H), 0.97 (d, 6H), 1.02–1.07 (m, 1H), 1.19–1.24 (m, 1H), 1.36–1.40 (m, 2H), 1.44–1.52 (m, 1H), 1.56–1.78 (m, 3H), 1.83–1.92 (m, 2H), 2.21 (app dd, 1H, J=14 Hz, J=17 Hz, 2.35–2.44 (m, 3H), 2.81–2.93 (m, 2H), 6.58 (d, 1H, J=2.4 Hz), 6.63 (dd, 1H, J=8.3 Hz, J=2.7 Hz), 7.13 (d, 1H, J=8.5 Hz).

Pharmaceutical Preparations

The novel steroidal estrogens according to the invention may be administered by transdermal patches, orally or intranasally.

The dosage will depend on the route of administration, the severity of the disease, age and weight of the patient and other factors normally considered by the attending physician, when determining the individual regimen and dosage level as the most appropriate for a particular patient.

The pharmaceutical preparation comprising a compound of the invention may be a patch, a tablet, a capsule or a nasal spray.

In a transdermal device, an estrogen compound of the invention is dissolved in suitable solvents (e.g. ethanol, propylene glycol) comprising a thickener. The patch further comprises a current backing membrane and a silicone release liner. The device may also be constructed with a rate control membrane.

When administered orally the estrogen compounds of the invention may be administered as a conventional tablet or gelatin capsule. The tablet may comprise usual tablet constituents, e.g. diluents (such as lactose), binders (such as polyvidone), lubricants (such as magnesium stearate) and disintegrants (such as microcrystalline cellulose). The estrogen compound may also be mixed with diluents and filled into gelatin capsules.

When administered intranasally by means of a nasal spray, the formulation is a suspension of the novel estrogens of the invention in water comprising a thickener, a surface active ingredient and a preservative.

Biological Evaluation

The anti-inflammatory and immunosuppressive potencies were evaluated in animal models for autoimmune diseases.

For rheumatoid arthritis the type II collagen induced arthritis (CIA) model in mice was used (Jansson, L., Holmdahl, R., Clin. Exp. Immunol. (1992), 89, 446–451).

Mouse CIA Model

In this model F1 generation (females) between B10Q and DBA/1 mice are used. The mice are ovariectomized two weeks before induction of arthritis.

Immunisation is performed using collagen type II (purified from rat chondrosarcoma) emulsified in Freunds complete adjuvant.

The treatanent is performed by subcutaneous administration of estrogen analogues (0.1 ml) in Miglyol oil vehicle or solutol. The mice are treated on day 14, 17, 21, 24, 28, and 32 respectively, after immunisation. Day 36 is the end of the experiment, and the arthritis symptoms start approximately on day 14–20.

Evaluation of sex-related effects is performed by observing the stage of estrus by vaginal smears 17, 21, 24, 30, and 36 days after immunisation. At day 36 which is the end of the experiment, the weight of the uterus is recorded.

The evaluation of the arthritic effect is performed by observing the joints of the paws and legs for swelling and erythema every third day after immunisation.

The development of arthritis was evaluated continuously for each group as the incidence (%) of affected animals. The cumulative incidence (area under the curve, "auc") was calculated in each group up to day 30. The anti-arthritic effect of estrogen treatment was expressed as the auc of treated animals relative the auc of the control group (auc$_{treated\ animals}$/auc$_{control}$, %), i.e. 100% denotes no anti-arthritic effect and 0% denotes total blockade of arthritic development. The antiarthritic effect is related in dose-response studies to the extent of uterine proliferation, and it is possible to estimate the difference in immunosuppressive/sex hormonal profiles.

The novel steroidal estrogens of the present invention, derivatives of 17-alkylidene-3,16-dihydroxy-estra-1,3,5 (10)-trienes, show very low "sex hormonal" activity while retaining their anti-inflammatory and immunosuppressive effects.

The Rat-CIA Model

Still another animal model for the evaluation of the anti-inflammatory and immunosuppressive effects is the rat CIA model.

In this model female rats of the Dark Agouti strain are used. The rats are ovariectomized two weeks before induction of arthritis.

Immunisation is performed using the same protocols as for CIA in mice, but with Freunds incomplete adjuvant.

Evaluation of the arthritic and sex-related effects are the same as in the mouse model. The length of the rat CIA-experiment is 21 days.

We claim:

1. A compound according to the formula I

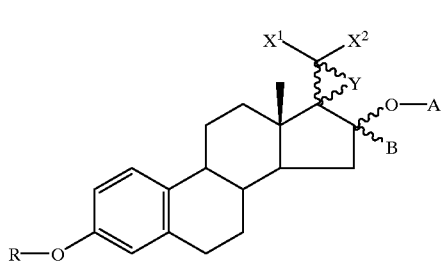

wherein

A is hydrogen, $C_2$–$C_{18}$ alkanoyl, ($C_6$ aryl)carbonyl, $C_2$–$C_{19}$ alkoxycarbonyl, or ($C_6$ aryloxy)carbonyl, or a protecting group;

B is hydrogen, methyl, or ethyl;

R is hydrogen, a straight, branched or cyclic $C_1$–$C_6$ alkyl, $C_2$–$C_{18}$ alkanoyl, ($C_6$ aryl)carbonyl, $C_2$–$C_{19}$ alkoxycarbonyl, ($C_6$ aryloxy)carbonyl, or a protecting group;

$X^1$ is hydrogen, methyl, ethyl or halogen;

$X^2$ is hydrogen, methyl, ethyl or halogen; and

Y is methylene or a single bond;

and pharmaceutically acceptable salts thereof;

the compounds (17E)-16α-Acetoxy-3-methoxy-19-norpregna-1,3,5 (10),17(20)-tetraene;

(17E)-16α-Hydroxy-3-methoxy-19-norpregna-1,3,5 (10),17(20)-tetraene; and (17E)-16β-Hydroxy-3-methoxy-19-norpregna-1,3,5 (10),17(20)-tetraene being excluded.

2. A compound according to claim 1, wherein

A is hydrogen or $C_{2-6}$ alkanoyl;

B is hydrogen or methyl;

R is hydrogen, a straight, branched or cyclic $C_{1-6}$ alkyl, $C_{2-18}$ alkanoyl, ($C_6$ aryl)carbonyl, $C_{2-19}$ alkoxycarbaonyl, ($C_6$aryloxy)carbonyl, or a protecting group;

$X^1$ is hydrogen, methyl, or fluorine;

$X^2$ is hydrogen, methyl, or fluorine; and

Y is a methylene group or a single bond.

3. A compound according to claim 1, wherein

A is hydrogen or $C_{2-6}$ alkanoyl;

B is hydrogen;

R is hydrogen, a straight, branched or cyclic $C_{1-6}$ alkyl, $C_{2-18}$ alkanoyl, ($C_6$ aryl)carbonyl, $C_{2-19}$ alkoxycarbonyl, ($C_6$aryloxy)carbonyl, or a protecting group;

$X^1$ is hydrogen or fluorine;

$X^2$ is hydrogen or fluorine; and

Y is a single bond or a methylene group.

4. A compound according to claim 1, wherein

A is hydrogen;

B is hydrogen;

R is hydrogen or $C_2$–$C_6$ alkanoyl;

$X^1$ is hydrogen;

$X^2$ is hydrogen;

Y is a single bond; and the 16-OH group is in the α-position.

5. A compound of claim 1, having the formula 3,16α-dihydroxy-17-methylene-estra-1,3,5(10)triene.

6. A therapeutic composition comprising the compound of claim 1 in a pharmaceutically acceptable carrier.

7. A method for treating rheumatoid arthritis or multiple sclerosis comprising administering to a patient in need thereof an affective amount of the compound of claim 1.

8. The method of claim 7, wherein

B is hydrogen;

$X^1$ is hydrogen or fluorine; and $X^2$ is hydrogen or fluorine.

9. The method of claim 7, wherein

A is hydrogen;

B is hydrogen;

R is hydrogen or $C_{2-6}$ alkanoyl;

$X^1$ is hydrogen;

$X^2$ is hydrogen;

Y is a single bond; and the 16-OH group is in the α-position.

10. The method of claim 7, wherein the compound has the formula 3,16α-dihydroxy-17-methylene-estra-1,3,5(10)triene.

11. The method of claim 7, wherein

A is hydrogen or $C_2$–$C_6$ alkanoyl;

B is hydrogen or methyl;

$X^1$ is hydrogen, methyl, or fluorine; and $X_2$ is hydrogen, methyl, or fluorine.

12. A method for treating multiple sclerosis comprising administering to a patient in need thereof an effective amount of the compound of claim 1.

13. The method of claim 12, wherein

A is hydrogen or $C_2$–$C_6$ alkanoyl;

B is hydrogen or methyl;

$X^1$ is hydrogen, methyl, or fluorine; and $X^2$ is hydrogen, methyl, or fluorine.

14. The method of claim 12, wherein

A is hydrogen or $C_2$–$C_6$ alkanoyl;

B is hydrogen;

$X^1$ is hydrogen or fluorine; and $X^2$ is hydrogen or fluorine.

15. The method of claim 12, wherein

A is hydrogen;

B is hydrogen;

R is hydrogen or $C_2$–$C_6$ alkanoyl;

$X^1$ is hydrogen;

$X^2$ is hydrogen;

Y is a single bond; and the 16-OH group is in the α-position.

16. The method of claim 12, wherein the compound has the formula 3,16α-dihydroxy-17-methylene-estra-1,3,5(10)triene.

* * * * *

Disclaimer 6,043,236—Palph Brattsand; Rikard Holmdahl; Liselotte Jansson; Marjana Loncar, all of Lund; Lars Pettersson, Sodra Sandby, all of Sweden. ESTROGENS. Patent dated March 28, 2000. Disclaimer filed September 4, 2001 by the assignee, AstraZeneca AB.

Hereby enters this disclaimer to all claims (1-16) of said patent.

*(Official Gazette, August 27, 2002)*